(12) United States Patent
Khopade et al.

(10) Patent No.: US 11,559,487 B2
(45) Date of Patent: Jan. 24, 2023

(54) DRUG LOADED NANORESIN PARTICLES

(71) Applicant: SUN PHARMA ADVANCED RESEARCH COMPANY LIMITED, Mumbai (IN)

(72) Inventors: Ajay Jaysingh Khopade, Baroda (IN); Arindam Halder, Baroda (IN); Shivam Umeshkumar Upadhyay, Baroda (IN)

(73) Assignee: SUN PHARMA ADVANCED RESEARCH COMPANY LIMITED, Mumbai (IN)

( * ) Notice: Subject to any disclaimer, the term of this patent is extended or adjusted under 35 U.S.C. 154(b) by 0 days.

(21) Appl. No.: 16/707,833

(22) Filed: Dec. 9, 2019

(65) Prior Publication Data

US 2020/0170951 A1 Jun. 4, 2020

Related U.S. Application Data

(63) Continuation of application No. 15/747,032, filed as application No. PCT/IN2016/050253 on Jul. 27, 2016, now abandoned.

(30) Foreign Application Priority Data

Jul. 27, 2015 (IN) .......................... 2841/MUM/2015

(51) Int. Cl.
| | | |
|---|---|---|
| *A61K 9/14* | (2006.01) | |
| *A61K 9/00* | (2006.01) | |
| *A61K 9/20* | (2006.01) | |
| *A61K 9/10* | (2006.01) | |
| *A61K 9/06* | (2006.01) | |
| *A61K 31/135* | (2006.01) | |
| *A61K 31/196* | (2006.01) | |
| *A61K 31/335* | (2006.01) | |
| *A61K 31/498* | (2006.01) | |
| *A61K 31/519* | (2006.01) | |
| *A61K 31/65* | (2006.01) | |
| *B82Y 5/00* | (2011.01) | |
| *A61K 47/38* | (2006.01) | |
| *A61K 47/32* | (2006.01) | |

(52) U.S. Cl.
CPC ............ *A61K 9/146* (2013.01); *A61K 9/0014* (2013.01); *A61K 9/06* (2013.01); *A61K 9/10* (2013.01); *A61K 9/2018* (2013.01); *A61K 31/135* (2013.01); *A61K 31/196* (2013.01); *A61K 31/335* (2013.01); *A61K 31/498* (2013.01); *A61K 31/519* (2013.01); *A61K 31/65* (2013.01); *A61K 47/32* (2013.01); *A61K 47/38* (2013.01); *B82Y 5/00* (2013.01)

(58) Field of Classification Search
None
See application file for complete search history.

(56) References Cited

U.S. PATENT DOCUMENTS

| | | |
|---|---|---|
| 4,380,590 A | 4/1983 | Chong et al. |
| 7,001,615 B1* | 2/2006 | Singh .................... A61K 9/0043 424/486 |
| 2005/0181017 A1* | 8/2005 | Hughes ................ A61K 9/0048 424/427 |
| 2008/0131484 A1 | 6/2008 | Robinson et al. |
| 2009/0098192 A1* | 4/2009 | Fuisz .................. A61K 47/6953 424/443 |
| 2010/0124565 A1* | 5/2010 | Spada ..................... A61P 27/06 514/249 |
| 2011/0136059 A1 | 6/2011 | Xiqiang |

FOREIGN PATENT DOCUMENTS

| | | |
|---|---|---|
| CA | 1161597 A1 | 1/1984 |
| JP | 2013075856 A | 4/2013 |
| WO | WO 91/13612 | 9/1991 |

(Continued)

OTHER PUBLICATIONS

International Search Report from International Application No. PCT/IN2016/050253, dated Nov. 7, 2016.
Guangfeng Liu, et al. Synthesis of monodispersed crosslinked nanoparticles decorated with surface carboxyl groups via soapless emulsion polymerization, Colloids and Surfaces A: Physicochem. Eng. Aspects 354 pp. 377-381 (2010).
Jiang Kai, et.al, "Synthesis of monodisperse crosslinked polystyrene microspheres", Pet.Sci.5: pp. 375-378 (2008).

(Continued)

*Primary Examiner* — Brian Gulledge
(74) *Attorney, Agent, or Firm* — Blank Rome LLP (57) ABSTRACT

The present invention relates to nano-resin particles that are suitable for pharmaceutical use and their use in the pharmaceutical field. The present invention provides nano-sized resin particles having a particle size distribution characterized in that $D_{90}$ value is between 200 nanometers to 900 nanometer and $D_{10}$ value is not less than 50 nanometers, wherein the nano-resin particles are in pure form and safe for pharmaceutical use. The present invention further relates to pharmaceutical compositions comprising these purified nano-resin particles and their use in the treatment of diseases.

The present invention further provides a process for preparing purified, nano-sized resin particles that are suitable for pharmaceutical use, the process comprising steps of: (i) washing an ion exchange resin and suspending in an aqueous liquid, (ii) subjecting the suspension of (i) to wet milling for a period such that the particles have a particle size distribution characterized in that the $D_{90}$ value is between 200 nanometers to 900 nanometers and $D_{10}$ value is not less than 50 nanometers, (iii) subjecting the suspension of (ii) to purification to remove impurities, (iv) drying the purified suspension to obtain nano-resin particles in the form of dry powder.

15 Claims, 1 Drawing Sheet

(56) References Cited

FOREIGN PATENT DOCUMENTS

| WO | WO9113612 | 9/1991 | | |
|---|---|---|---|---|
| WO | WO-2012063257 A2 | 5/2012 | | |
| WO | WO-2015192030 A1 | 12/2015 | | |
| WO | WO 2016/016908 A1 | 2/2016 | | |
| WO | WO201016908 | 2/2016 | | |
| WO | WO-2017017699 A1 * | 2/2017 | ........... | A61K 31/135 |

OTHER PUBLICATIONS

Chang-Moon Lee, et al., "Rosin nanoparticles as a drug delivery carrier for the controlled release of hydrocortisone", Biotechnology Letters 27: pp. 1487-1490 (2005).

M. V. Srikanth, et.al, "Ion-Exchange Resins as Controlled Drug Delivery Carriers", J. Sci. Res. 2 (3), pp. 597-611 (2010).

Extended European Search Report for Corresponding Application No. 16829974.1 dated Mar. 13, 2019.

Prajapati, et al., Formulation and Evaluation of Sublingual Tablets Containing Sumatriptan Succinate, International Journal of Pharmaceutical Investigation, 2012, 2:162-168.

\* cited by examiner

DRUG LOADED NANORESIN PARTICLES

FIELD OF INVENTION

The present invention relates to nano-resin particles that are suitable for pharmaceutical use and their use in the pharmaceutical field.

BACKGROUND OF THE PRESENT INVENTION

There is plethora of prior art on the use of resins, particularly ion exchange resin, to complex the drug to meet various objectives such as to make a taste masking composition, to improve chemical stability of a drug, controlling the release of the drug etc. Ion exchange resins are commercially available, but the average particle size is in micrometer size, such as for example in the range of 50 to 150 microns. Till date, ion exchange resins are known to be available only in the micrometer size range, and not in nanometer range which may be suitable for pharmaceutical use. This may be due to the fact that while reducing the particle size of the ion exchange resins, the resin material tends to break down forming impurities which raise safety concerns or toxicity concerns such as irritation to the mucosa, skin irritation, hypersensitivity, allergic reactions and so on. For example, the limit for water extractable impurities for Amberlite IRP-64 is not more than 2%. The present inventors faced with a problem of unacceptable higher levels of water extractable impurities as high as 3% and more than 10 ppm of organic extractable impurities, when the resins were reduced to a particle size in the nanometer range.

SUMMARY OF THE INVENTION

The present inventors arrived at ion exchange nano-resin particles having average particle size range in nano-meter range and low levels of water extractable and organic impurities. The milled resin particles have a particle size distribution such that the $D_{90}$ value is between 200 nanometers to 900 nanometer and $D_{10}$ value is not less than 50 nanometers. This fraction of the resin is particularly free of very fine particles such as particles having size of less than 50 nanometers. The inventors found that such a resin of the defined particle size distribution such that $D_{90}$ value is between 200 nanometers to 900 nanometer and $D_{10}$ value is not less than 50 nanometers, could be obtained by a process which is less time consuming, economical and cost effective. Lowering the content of the very fine particles that are less than 50 nm enabled the inventors to purify the resins. It was found by the inventors that it was extremely difficult to obtain purified form of a resin that includes very fine particles having $D_{10}$ value of less than 50 nanometers. This was because during the purification of the milled resins to remove the water extractable impurities by passing through an ultrafiltration membrane, there was a problem of clogging of the membrane because of the presence of fine particles such as those which have $D_{10}$ value of less than 50 nanometers, making the process very time consuming and not feasible in commercial scale.

The present invention provides nano-sized resin particles suitable for pharmaceutical use, wherein the resin particles have a particle size distribution such that $D_{90}$ value is between 200 nanometers to 900 nanometers and $D_{10}$ value is not less than 50 nanometers. The purified nanoresins of the present invention contain water extractable impurities of less than 1% by weight. The individual unknown organic impurity is not more than 1 ppm and total unknown organic impurities are not more than 3 ppm. Such a purified form of the nano-resin particles of the present invention finds applicability as efficient drug carriers, where drugs are adsorbed onto the surface of the resin particles. These drug loaded nano-resin particles are suitable for incorporation into pharmaceutical dosage forms meant for topical, ophthalmic, dermal, peripheral, oral, sublingual, nasal, otic, peripheral, rectal or vaginal delivery.

In one aspect, the present invention provides use of a pharmaceutical composition comprising drug loaded nano-resin particles having a particle size distribution characterized in that the $D_{90}$ value is between 200 nanometers to 900 nanometers and $D_{10}$ value is not less than 50 nanometers, in the treatment of a disease by delivering the drug via dermal or oral or sublingual route of administration. The drug loaded nano-resin particles used in the treatment of a disease by delivering the drug via dermal or oral or sublingual route of administration contain water extractable impurities of not more than 1% by weight of the total resin and total unknown organic impurities of not more than 3 ppm.

In one aspect the present invention provides an aqueous suspension dosage form comprising drug loaded nanoresin particles having a particle size distribution characterized in that the $D_{90}$ value is between 200 nanometers to 900 nanometers and $D_{10}$ value is not less than 50 nanometers, a suspending agent and an aqueous vehicle, and its use in the treatment of a disease by delivering the drug via dermal or oral or sublingual route of administration.

In another aspect, the present invention provides a semi-solid dosage form comprising drug loaded nanoresin particles having a particle size distribution characterized in that the $D_{90}$ value is between 200 nanometers to 900 nanometers and $D_{10}$ value is not less than 50 nanometers, in an aqueous or a non-aqueous vehicle, and its use in the treatment of a disease by delivering the drug via dermal route of administration. The semisolid dosage form can be in the form of a cream, ointment, lotion, emulsion, suspension or a gel.

The present invention also provides nano-sized resin particles suitable for pharmaceutical use, wherein the resin particles have a particle size distribution such that $D_{90}$ value is between 200 nanometers to 900 nanometers and $D_{10}$ value is not less than 50 nanometers, prepared by a process comprising steps of:
i. washing an ion exchange resin and suspending in an aqueous liquid,
ii. subjecting the suspension of (i) to wet milling for a period such that the particles have a particle size distribution characterized in that the $D_{90}$ value is between 200 nanometers to 900 nanometers and $D_{10}$ value is not less than 50 nanometers,
iii. subjecting the suspension of (ii) to purification to remove impurities,
iv. drying the purified suspension to obtain nano-resin particles in the form of dry powder.

The present invention further relates to a process of preparing nano-sized resin particles having a particle size distribution such that $D_{90}$ value is between 200 nanometers to 900 nanometer and $D_{10}$ value is not less than 50 nanometers, the process comprising steps of:
i. washing an ion exchange resin and suspending in an aqueous liquid,
ii. subjecting the suspension of (i) to wet milling for a period such that the particles have a particle size distribution characterized in that the $D_{90}$ value is between 200 nanometers to 900 nanometers and $D_{10}$ value is not less than 50 nanometers, iii. subjecting the suspension of (ii) to purification to remove impurities, iv. drying the purified suspension to obtain nano-resin particles in the form of dry powder.

DETAILED DESCRIPTION OF THE INVENTION

The particle size is expressed in terms of particle size distribution including values of $D_{90}$, $D_{50}$ and $D_{10}$, as measured by Malvern Mastersizer, which is based on laser light diffraction technique. The particle size distribution may alternatively be measured using other techniques such as photon correlation spectroscopy, sedimentation field flow fractionation, or disk centrifugation.

The water extractable impurities and organic impurities like individual unknown impurity and total unknown organic impurities, of the resin are the impurities that are formed during milling and whose chemical structure is not known. Such impurities may be determined by techniques known in the art. In one aspect, the water extractable impurities are determined by weighing the dried water extract of the resin. The organic impurities may be determined by extracting the resin with an organic solvent and determining the impurities content by weighing the dried organic extract of the resin. It is possible to determine the impurity levels by any other means such as HPLC, mass spectroscopy etc.

'Reversible Clusters' of drug loaded nano-resin particles, as described herein means that the individual drug loaded nanoresin particles when formulated into an aqueous suspension along with suspending agents, form aggregates or agglomerates having mean size of about 2 micrometers or greater, which upon application of mild shear, deagglomerate or decluster into individual drug loaded nano-resin particles. The mild shear that can cause deagglomeration or declustering of the reversible clusters include mild shear such as that observed upon blinking of eye or contact with aqueous environment of mucous membranes, saliva, gastrointestinal flora, mild rubbing or application during topical skin application and the like.

According to one aspect of the invention, the resin is an ion exchange resin. The ion exchange resins are covalently bound in repeating positions on the resin chain. These charged groups associate with other ions of opposite charge. The ion exchange resin may be cationic or anionic in nature. Depending on whether the mobile counter ion is a cation or an anion, it is possible to distinguish between cationic and anionic exchange resins. The ion exchange resins commercially available in the market have a mean particle size in micron range such as for example between 50 microns to 150 microns. The matrix in cationic exchangers carries ionic groups such as sulfonic, carboxylate and phosphate groups. The matrix in anionic exchangers carries primary, secondary, tertiary or quaternary ammonium groups. The resin matrix determines its physical properties, its behavior towards biological substances, and to a certain extent, its capacity.

Cationic drugs such as brimonidine have a positive charge, so they can bind with cation exchange resins. Preferred cation exchange resin includes sulfonic acid exchangers. In general, they are cross-linked polystyrenes with sulfonic acid groups that have been introduced after polymerization by treatment with sulfuric acid or chlorosulfonic acid.

Suitable cation exchange resins that may be used in the present invention includes, but are not limited to, sodium polystyrene divinyl benzene sulphonate, such as marketed by Rohm and Haas, under the trade name Amberlite™ IRP 69; polacrilex resin which is derived from a porous copolymer of methacrylic acid and divinylbenzene, such as marketed by Rohm and Haas, under the trade name Amberlite™ IRP 64; polacrilin potassium, which is a potassium salt of a cross linked polymer derived from methacrylic acid and divinylbenzene, such as marketed by Rohm and Haas, under the trade name Amberlite™ IRP 88. The resins marketed by the company Ion Exchange India Ltd., under the tradenames such as INDION™234; INDION™264; INDION™ 204; INDION™ 214 may also be used.

In one embodiment, the preferred resin used in the present invention is Amberlite IRP69 which is derived from a sulfonated copolymer of styrene and divinyl benzene. Amberlite IRP-69 is a pharmaceutical grade strong cation exchange resin and structurally a polystyrene sulfonic acid resin cross-linked with divinyl benzene, i.e. polystyrene divinyl benzene sulfonate. Amberlite IRP-69 resin is available commercially from Rhom & Haas Company. The mobile or exchangeable cation in the resin is sodium, which can be exchanged for, or replaced by, cationic (basic) species.

In some embodiments of the present invention, positively charged cationic drug is bound to the negatively charged sulfonic acid groups of the Amberlite resin.

In some embodiments of the present invention, the ion-exchange resin is an anion exchange resin and the drug is anionic in nature. The matrix in anionic exchange resin generally carries primary, secondary, tertiary or quaternary ammonium groups. Suitable anion exchange resins that may be used in the present invention includes, but are not limited to, cholestyramine resin, such as marketed by Rohm and Haas, under the trade name Duolite™ AP143/1093; INDION™860, which is a macroporous weakly basic anion resin having a tertiary amine functionality attached to a polymeric styrene divinyl benzene matrix; INDION™GS400, which is strong base Type II anion exchange resin, based on cross linked polystyrene matrix with benzyl dimethyl ethanol amine functional groups.

The present invention provides nano-resin particles having a particle size distribution characterized in that the $D_{90}$ value is between 200 nanometers (nm or nms) to 900 nanometers (nm or nms), such as 250, 300, 350, 400, 450, 500, 550, 600, 650, 700, 750, 800 or 850 nanometers, preferably between 250 nms to 700 nms, more preferably between 300 nms to 500 nms. The nano-resin particles have a $D_{50}$ value between 75 nms to 300 nms, such as 80, 85, 90, 95, 100, 125, 150, 175, 200, 225, 250 or 275 nanometers, preferably between 100 nms to 250 nms, more preferably between 120 nms to 175 nms. The nano-resin particles have a $D_{10}$ value of not less than 50 nanometers, preferably between 50 nms to 200 nms, such as 60 nms, 65 nms, 70 nms, 75 nms, 80 nms, 85 nms, 90 nms, 95 nms, 100 nms, 110 nms, 120 nms, 130 nms, 140 nms, 150 nms, 160 nms, 170 nms, 180 nms or 190 nms, more preferably between 60 nms to 150 nms.

In one embodiment, the present invention provides nano-resin particles having a particle size distribution characterized in that the $D_{90}$ value is between 200 nms to 900 nms, and $D_{10}$ value is not less than 50 nanometers.

In one embodiment, the present invention provides nano-resin particles having a particle size distribution characterized in that the $D_{90}$ value is between 200 nms to 900 nms, $D_{50}$ value is between 75 nms to 300 nms and $D_{10}$ value is not less than 50 nanometers.

In one embodiment, the present invention provides nano-resin particles having a particle size distribution characterized in that the $D_{90}$ value is between 250 nms to 700 nms, $D_{50}$ value is between 100 nms to 250 nms and $D_{10}$ value is between 60 nms to 150 nanometers, for example, 65 nm, 70 nms, 71 nms, 72 nms, 73 nm, 74 nms, 75 nm, 80 nms, 85 nms, 90 nms, 95 nms, 100 nms, 105 nms, 110 nms, 120 nms, 130 nms, 140 nms or 150 nms.

The 'drugs' according to the present invention include therapeutically active ingredients that are capable of forming a salt with an acid or an alkali, and includes ionizable therapeutically active ingredients.

According to one aspect, drugs include ionizable drugs that can form salts with acids, known as cationic drugs.

According to another aspect, drugs include ionizable drugs that can form a salt with a base or an alkali, known as anionic drugs.

Non limiting examples of the drugs according to the present invention include therapeutically active agents selected from, but not limited to antiglaucoma agents; antibiotics or anti-infective agents; anti-allergic agents; antihistamines; analgesic agents; anti-inflammatory agents; steroids; non-steroidal anti-inflammatory agents; decongestant; anaesthetic agents; mydriatic agents, analeptic agents; antiasthmatic agents; antiarthritic agents; anticancer agents; anticholinergic agents; anticonvulsant agents; antidepressant agents; antiemetic agents; antihelminthic agents; antidiabetic agents; antidiarrheal agents; antihyperlipidemic agents; antihypertensive agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; anorexic agents; attention deficit disorder and attention deficit hyperactivity disorder drugs; cardiovascular agents including calcium channel blockers, antianginal agents, central nervous system agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizers; vasodilators; beta-agonist etc. These include drugs that are suitable for the treatment of disorders of the eye, like antiglaucoma agents, such as beta-blockers, carbonic anhydrase inhibitors, alpha-adrenergic agonists, prostaglandins, parasympathomimetics and cholinesterase inhibitors.

Non-limiting examples drugs that may be used include, latanoprost, travoprost, bimatoprost, tafluprost, isopropyl unoprostone, 8-isoprostaglandin-E2, timolol, levobunolol, befundol, metipranolol, carteolol, betaxolol, levobetaxolol, timolol, befunolol, labetalol, propranolol, metaprolol, bunalol, esmalol, pindolol, hepunolol, metipranolol, celiprolol, azotinolol, diacetolol, acebutolol, atenolol, isoxaprolol, brinzolamide, dorzolamide, acetazolamide, methazolamide, dichlorophenamide, brimonidine, dipivefrine, clonidine, p-aminoclonidine, p-acetoamidoclonidine, apraclonidine, physostigmine, ecothiopate, pilocarpine, demecarium, moxifloxacin, besifloxacin, gentamicin, neomycin; erythromycin, ciprofloxacin, polymyxin B, beta-lactam antibiotics, tetracycline, minocycline, doxycycline, chlortetracycline, olopatadine, emedastine, azelastine, epinastine, levocabastine, bepotastine, pheniramine, chlorpheniramine, epinephrine, proepinephrine, norepinephrine, pyrilamine, dextromethorphan, dexamethasone, prednisolone, amitryptilline, ketotifen, oxymetazoline, phenylephrine, naphazoline, antazoline, proparacaine, lidocaine, cyclopentolate, diclofenac, bromfenac, sulfacetamide, flurbiprofen, ketorolac, lodoxamide, sulfacetamide, methotrexate, cromolyn, pemirolast or their pharmaceutically acceptable salts or mixtures thereof. Other drugs that can form a complex with ion exchange resins may also be used and are within the scope of this invention.

In one embodiment, the weight ratio of resin to drug may range from 0.1:1 to 1:0.1, such as 0.2:1 to 1:0.2, 0.3:1 to 1:0.3, 0.4:1 to 1:0.4, 0.5:1 to 1:0.5, 0.6:1 to 1:0.6, 0.7:1 to 1:0.7, 0.8:1 to 1:0.8 or 0.9:1 to 1:0.9, more preferably from 0.3:1 to 1:0.3. In one preferred embodiment, the weight ratio between the nano-resin particles and drug is about 1:1.

The nano-resin particles of the present invention in dried form have water content of not more than 15% by weight, such as not more than 14.0, 13.0, 12.0, 11.0, 10.0, 9.0, 8.0, 7.0, 6.0, 5.5, 5.0, 4.5, 4.0, 3.5, 3.0, 2.5, 2.0, 1.5, 1.0 or 0.5%, preferably not more than 10%, more preferably not more than 5% by weight.

The nano-resin particles of the present invention are in purified form, suitable for pharmaceutical use. The nano-resin particles in a purified form contain safe amounts of water extractable impurities and organic impurities like individual unknown impurity and total unknown organic impurities. The purified nanoresins contain water extractable impurities of less than 1% by weight, individual unknown organic impurity not more than 1 ppm (parts per million) and total unknown organic impurities not more than 3 ppm.

The purified nano-resin particles of the present invention are safe for pharmaceutical use. The safety has been tested and demonstrated in one of the most sensitive external tissue of the body i.e. the ocular tissue. The nano-resin particles were used to formulate an ophthalmic suspension of drug loaded nano-resinate particles. The test drug was brimonidine. The ophthalmic suspension was subjected to safety studies by daily ocular administration to the eyes of New-Zealand White rabbits for consecutive 14 days. The effect of various dose levels was studied, the dose levels varying from low dose (60 µL/animal/day i.e. 30 µL per eye/time ×1 times a day) to mid dose (180 µL/animal/day i.e. 30 µL per eye/time ×3 times a day) to high dose (360 µL/animal/day i.e. 30 µL per eye/time ×6 times a day). Several safety related test parameters were evaluated, including—Daily Clinical Signs and Mortality; Detailed Clinical Sign Observation; Body Weights; Ophthalmoscopy and Necroscopy. The details of these test parameters along with the results are described below. Besides these, other parameters were also evaluated including: clinical pathology, histology, biochemistry, prothrombin time and urine analysis. It was observed that there occurs no mortality in animals of any dose group. No test item related clinical signs were observed during daily or detailed clinical sign observations. No test item related adverse changes noticed in body weights, percent body weight changes, ophthalmoscopy, hematology, biochemistry, urine, absolute organ weights and relative organ weights of males and females. In males and females, no test item related macroscopic or microscopic lesions were observed in any organ including eyes in any dose group.

Another study was performed which validated the safety of purified nano-resin particles of the present invention. This long term study evaluated the safety of an ophthalmic suspension comprising brimonidine loaded nano-resin particles, after multiple daily instillation for 30 consecutive days in New Zealand white rabbits. No test item related changes were noticed for hemodynamic parameters in any animal during the study period. No mortality was observed in any dose group. No test item related changes were noticed in detailed clinical sign observations, body weights, percent body weight changes, ophthalmoscopy, hematology and biochemistry of animals. Therefore, based on these observations, the ocular NOAEL (no observed adverse effect levels) of 0.35% w/v Brimonidine tartrate ophthalmic suspension, according to one embodiment of the present invention, was established to be about 0.33 mg/kg/day in New Zealand White Rabbits. The NOAEL for systemic effects was also 0.33 mg/kg/day. This is about 30 times more than the human maximum dose of brimonidine in mg/m$^2$ basis. It is concluded that ocular delivery of test item at 30 µL/eye in both eyes, up to maximum 6 times per day for 30 days consecutive daily administration, did not produce any adverse effects in the eye with no local toxicity at the site of application as well as no systemic toxicity.

Besides this study, the present inventors also carried out biological reactivity tests wherein the nano-resin particles of the present invention (Example 1) were subjected to in vivo and in vitro biological reactivity tests to determine their biological reactivity. The in vivo biological reactivity of milled resin extract was assessed by Intracutaneous test in New Zealand White Rabbits as per procedure mentioned in USP <88> biological reactivity, and it was observed that the milled nano-resin extract complied with USP "Intracutaneous test" requirements. The in-vitro biological reactivity of milled resin extract was assessed by Agarose diffusion Assay in NCTC clone 929 (L cell; L-929) ATCC. No biological reactivity of mammalian cell cultures following milled resin extract was observed.

These safety experiments validate the safe and non-toxic nature of the nano-resin particles of the present invention and also supported their suitability for use in pharmaceutical dosage forms such as ophthalmic, dermal, sublingual, buccal, peroral, nasal, otic etc.

The present invention provides a pharmaceutical composition comprising nano-resin particles having a particle size distribution characterized in that the $D_{90}$ value is between 200 nanometers to 900 nanometers and $D_{10}$ value is not less than 50 nanometers and a pharmaceutically active agent.

The present invention in one aspect provides, use of a pharmaceutical composition comprising drug loaded nano-resin particles having a particle size distribution characterized in that the $D_{90}$ value is between 200 nanometers to 900 nanometers and $D_{10}$ value is not less than 50 nanometers in the treatment of a disease by delivering the drug via dermal or oral or sublingual route of administration. The nano-resin particles are further characterized in having $D_{50}$ value between 75 nanometers to 300 nanometers. The nano-resin particles used in the pharmaceutical compositions contain water extractable impurities of not more than 1% by weight of the total resin, and total unknown organic impurities of not more than 3 ppm.

The present invention further provides use of a semisolid dosage form comprising drug loaded nanoresin particles having a particle size distribution characterized in that the $D_{90}$ value is between 200 nanometers to 900 nanometers and $D_{10}$ value is not less than 50 nanometers, in an aqueous or a non-aqueous vehicle, in the treatment of a disease by delivering the drug via dermal route of administration. The semisolid dosage form may be one of a cream, an ointment, lotion, emulsion, suspension or a gel. The semi-solid dosage forms are suitable for the treatment of dermal disorders such as atopic dermatitis, acne, rosacea, alopecia, impetigo, secondary skin infections, inflammatory disorders, dermatitis, lupus erythematosus, psoriasis, plague, keratosis, actinic keratosis, seborrheic keratosis, eczema, hives, warts, seborrhea, shingles, scabies, skin lesions, vitiligo, hyperhidrosis, ichthyosis, bacterial, fungal or viral infections of the skin, etc.

In one embodiment, the dosage form is suitable for application on scalp, for the treatment of disorders like alopecia. Suitably in this embodiment, the drug that may be used includes brimonidine, bromfenac, doxycycline, etc.

The present invention in one aspect provides liquid dosage form comprising drug loaded nanoresin particles having a particle size distribution characterized in that the $D_{90}$ value is between 200 nanometers to 900 nanometers and $D_{10}$ value is not less than 50 nanometers, in an aqueous or a non-aqueous liquid vehicle.

The present invention in one aspect provides use of an ophthalmic composition comprising drug loaded nanoresin particles having a particle size distribution characterized in that the $D_{90}$ value is between 200 nanometers to 900 nanometers and $D_{10}$ value is not less than 50 nanometers, in an aqueous or a non-aqueous vehicle, in the treatment of a disorder of the eye, by delivering the drug via ophthalmic route of administration. The ophthalmic composition is suitable for the treatment of diseases or disorders of the eye. In some embodiment, the ophthalmic composition is suitable for the treatment of glaucoma, eye infection, conjunctivitis, ptyerigium. The ophthalmic dosage form may be a suspension, ointment, gel or other suitable ophthalmic compositions.

The present invention in one aspect provides use of an aqueous suspension dosage form comprising drug loaded nanoresin particles having a particle size distribution characterized in that the $D_{90}$ value is between 200 nanometers to 900 nanometers and $D_{10}$ value is not less than 50 nanometers, a suspending agent and an aqueous vehicle, in the treatment of a disease by delivering the drug via dermal or oral or sublingual route of administration.

In one embodiment, the pharmaceutical composition is in the form of an aqueous suspension dosage form comprising drug loaded nanoresin particles having a particle size distribution characterized in that the $D_{90}$ value is between 200 nanometers to 900 nanometers and $D_{10}$ value is not less than 50 nanometers, a suspending agent and an aqueous vehicle, suitable for the treatment of a disease by delivering the drug via dermal or oral or sublingual route of administration. The suspending agent used may be selected from an anionic polymer, a non-ionic polymer or mixtures thereof. A cationic polymer may also be used. The anionic polymers may be selected from the group consisting of polymers of acrylic acid like carboxyvinyl polymer or carbomer, also known as carbopols. Various grades of carbomers including carbopol 934P, 974, 1342 and the like may be used in the present invention. The polymers of acrylic acid may be present in the aqueous suspension of the present invention in an amount ranging from about 0.01% to 0.5% weight by volume of the suspension. Other anionic polymers that can be used include, but are not limited to, sodium hyaluronate; sodium carboxymethylcellulose; guargum; chondroitin sulphate; sodium alginate. Particularly, the preferred anionic polymers that may be used include carbopol 974P. This anionic polymer is most preferably used in an amount of 0.1% w/v of the suspension.

The non-ionic polymers that can be used according to the present invention may be selected from the group consisting of non-ionic polymers such as polyvinyl pyrrolidone, soluplus-a polyvinyl caprolacatam-polyvinyl acetate-PEG graft co-polymer, poloxamers, polyvinyl alcohol, polypropylene glycol, cellulose derivatives like hydroxyethylcellulose, hydroxypropyl cellulose, hydroxypropyl methylcellulose, methyl cellulose, ethyl cellulose and the like. The non-ionic polymers may be present in the aqueous suspension of the present invention in an amount ranging from about 0.1% to about 5.0% weight by volume of the suspension. The preferred non-ionic polymers that may be used include hydroxypropyl methylcellulose and polyvinylpyrrolidone. Various pharmaceutically acceptable grades of hydroxypropyl methylcellulose (also known as hypromellose or HPMC or Methocel) and polyvinylpyrrolidine (also known as povidone or PVP or plasdone) may be used. The preferred grades of polyvinylpyrrolidine which can be used in the suspensions of the present invention include PVP K-30, PVP K-25, PVP K-50; PVP K-60 and PVP K-90. It may be present in the aqueous suspension in an amount ranging from about 0.5% to about 3.0% weight by volume of the suspension. The most preferred grade is PVP K-90, whose 10% w/v aqueous solution has a dynamic viscosity in the range of about 300.0 cps to about 700.0 cps at 20° C., and has an approximate molecular weight of about 1,000,000 to 1,500,000. In preferred embodiment, polyvinylpyrrolidine PVP K-90 is used in an amount of 1.2% w/v of the suspension. The preferred grades of hydroxypropylmethylcellulose which may be selected to be used in the aqueous suspensions of the present invention include, but is not limited to METHOCEL E, (USP grade 2910/HYPROMELLOSE 2910); METHOCEL F, (USP grade 2906/HYPROMELLOSE 2906); METHOCEL A15 (Premium LV); METHOCEL A4C (Premium); METHOCEL A15C (Premium); METHOCEL A4M (Premium), HPMC USP Grade 1828 and the like. It may be present in the suspension dosage form in an amount ranging from about 0.5% to about 3.0% weight by volume of the suspension. In most preferred embodiment, the aqueous suspension comprises Hypromellose 2910 in an amount of 0.3% w/v. As auxillary to the suspending agents, the flocculation of nanoresin particles may also be assisted by electrolytes.

The liquid dosage forms such as the aqueous suspension, according to the present invention may comprise other pharmaceutically acceptable excipients such as pH adjusting agents, buffers, chelating agents, preservatives, antioxidants, one or more osmotic agents/tonicity adjusting agents, colouring agents, sweetners, flavouring agents, preservative adjuvants, etc. The pharmaceutically acceptable excipients can be selected from those provided in the text book— Remington: The Science and Practice of Pharmacy, $22^{nd}$ Edition. The excipients may be used in suitable amounts, which can be readily determined by one of ordinary skill in the art, so as to get compositions having desired properties.

In one particular embodiment, the drug-loaded nano-resin particles are formulated into a suspension dosage form along with a suspending agent and an aqueous vehicle. When the drug particles are loaded onto the nano-sized resin particles, and formulated into an aqueous suspension with a suspending agent, a non-ionic polymer and an aqueous vehicle, surprisingly the inventors found that the drug-loaded nano-sized drug particles tend to agglomerate into a cluster, however, upon application of a shear, these clusters convert back into the individual drug loaded nano-sized drug particles having a particle size distribution such that $D_{90}$ value is between 200 nms to 900 nms and $D_{10}$ value is not less than 50 nms. The clusters are reversible clusters, which upon application of shear, deagglomerate or deaggregate to form individual drug loaded nanoresin particles. This is particularly important as there occurs no irreversible agglomeration, which can otherwise cause change in the particle size and impact the stability and bioavailability of the drug.

Qualitatively, the declustering can be observed by microscopy (Morphology G3S-ID Instrument, Make: Malvern) by observing sheared (by smearing) and unsheared samples onto the glass slide. Quantitatively, the $D_{50}$ of the clusters can be measured using Malvern Mastersizer before the application of shear. Other known means for determining particle size distribution/$D_{50}$ may alternatively be used.

The suspension of clusters is subjected to shear by placing in a sonication bath and using sonication frequency of about 33±3 kHz for 5 seconds, and a sample withdrawn to measure the particle size distribution using Malvern Mastersizer. Following intervals of 1 minute each, the process is repeated 5 times. The particle size distribution data before application of shear and upon application of shear at various time intervals is presented in Example 4, FIGS. 2-7. The particle size distribution of the nanoresin particles may be considered as the particle size distribution obtained after the suspension has been subjected to 5 pulses of frequency of 33±3 KHz with intervals of 1 minute each, as described above. During particle size analysis, the sonication means of the instrument are not used.

In one aspect, the present invention thus provides a suspension dosage form comprising drug loaded nanoresin particles having a particle size distribution characterized in that the $D_{90}$ value is between 200 nanometers to 900 nanometers and $D_{10}$ value is not less than 50 nanometers, a suspending agent and an aqueous vehicle, wherein the drug loaded nanoresin particles are characterized by a property of forming reversible clusters having a $D_{50}$ value of at least 2 micrometer.

In one particular embodiment, the nano-resin particles of the present invention are used for formulating an ophthalmic composition. It has been observed that an ophthalmic formulation comprising drug-loaded nanoresin particles of the present invention, show complete drug loading and at the same time, the drug release takes place at desired rate, which is important for an ophthalmic formulation where the residence time in the eye is very low. At the same time, the nano-resin particles are able to interact with the mucin layer in the eye, which improves overall retention and drug diffusion. This leads to enhance ocular bioavailability and reduction in dose and frequency of administration to achieve the desired therapeutic efficacy.

The liquid dosage forms, particularly the aqueous suspensions according to the present invention have a viscosity ranging from about 1 cps to 4000 cps, preferably about 5 cps to 400 cps such as 10, 15, 20, 25, 30, 35, 40, 45, 50, 55, 60,65,70, 75, 80, 85, 90, 95, 100, 120, 140, 160, 180, 200, 220, 240, 260, 280, 300, 320, 340, 360 or 380 cps. The viscosity may be measured by known techniques and instruments such as by Brookfield viscometer, under standard conditions. The aqueous suspensions according to one embodiment of the present invention, is such that it maintains its viscosity upon topical application to the mucosal cavity such as instillation into the eye. The viscosity does not change substantially upon coming in contact with the mucous fluid such as for example eye fluid that contains various ions such as sodium, potassium, calcium, magnesium, zinc, chloride, and bicarbonate.

In another aspect, the pharmaceutical composition is a semisolid dosage form comprising drug loaded nanoresin particles having a particle size distribution characterized in that the $D_{90}$ value is between 200 nanometers to 900 nanometers and $D_{10}$ value is not less than 50 nanometers, in an aqueous or a non-aqueous vehicle, suitable for the treatment of a disease by delivering the drug via topical route of administration. The semisolid dosage form may be one of a cream, an ointment, lotion, emulsion, suspension, paste, liniment, hydrogel or a gel.

The semisolid dosage forms or topical compositions may include excipients such as, but not limited to, wetting agents like cationic, anionic or non-ionic surfactant, non-aqueous vehicles, oils, waxes, penetration enhancing agents, antioxidants, preservatives, viscosity modifier, anti perspirant, antistatic agent, chelating agent, colorant, diluent, humectant, occlusive agent, perfuming agent, sunscreen, or other agents suitable for topical pharmaceutical compositions. Any suitable excipient/agent in each group that is suitable for topical pharmaceutical application may independently be used. Such suitable pharmaceutically acceptable excipients may be selected from those provided in the test book—Remington: The Science and Practice of Pharmacy, $22^{nd}$ Edition. The excipients may be used in suitable amounts known, which can be readily determined by one of ordinary skill in the art, so as to get compositions having desired properties.

In one particular embodiment, the pharmaceutical composition is a semisolid dosage form comprising drug loaded nanoresin particles having a particle size distribution characterized in that the $D_{90}$ value is between 200 nanometers to 900 nanometers and $D_{10}$ value is not less than 50 nanometers, in non-aqueous vehicle, suitable for the treatment of a disease by delivering the drug via dermal route of administration. The semisolid dosage form is preferably a cream or an ointment or a suspension or a gel. Such semisolid dosage forms comprising drug incorporated in nano-resin particles and formulated in non-aqueous vehicles are particularly suitable for incorporating, stabilizing and delivery of drugs that are susceptible to degradation in the presence of water or aqueous environment. Such drugs include but are not limited to minocycline, doxycycline, tetracycline, oxytetracycline, demeclocycline, lymecycline, meclocycline, methacycline, rolitetracycline, chlorotetracycline or tigecycline or pharmaceutically acceptable salts or mixtures thereof. The semisolid dosage forms according to this embodiment are useful in the treatment of disorders of the skin, particularly acne, rosacea, impetigo or a skin disease caused by bacteria.

The non-aqueous semisolid dosage form includes one or more non-aqueous vehicles that may be selected from silicon fluids like silicones, silicone derivatives or siloxanes, for example linear or cyclic alkyl siloxanes, aryl siloxanes, alkylether siloxanes, haloalkyl siloxanes, polycycloxanes, siloxane polymers, other functionalized siloxanes and mixtures thereof; non-volatile oil such as mineral oil, paraffin oil, castor oil, olive oil, seasom oil, soybean oil, peanut oil, coconut oil, avocado oil, jojoba oil, grape seed oil, jojaba oil, corn oil, cottonseed oil, white petrolatum, white soft paraffin, shea butter, triglycerides like labrafac, triacetin, capric/caprylic triglyeride, octyl dodecanol, diisopropyl adipate, light mineral oil and the like and mixtures thereof. It may further include other agents like wetting agents, emollients, gelling agents, viscosity builders, a penetration enhancer, an antioxidant, a preservative or other non-aqueous pharmaceutically acceptable excipients that are suitable for topical application. The wetting agent or surfactants may be selected from, but not limited to silicon based surfactant, non-ionic surfactants like Sorbitan esters (such as Span®80); Sucrose stearic acid esters; glyceryl monostearate, glyceryl monooleate, macrogolglycerol; hydroxy stearates (PEG 7 hydrogenated castor oil), PEGS castor oil and the like and mixtures thereof. A penetration enhancer may be selected form but not limited to isopropyl myristate, isopropyl palmitate, oleic acid etc. The antioxidant that may be used may be selected from butylated hydroxy anisole, butylated hydroxy toluene, tocopherol succinate, propyl gallate, tocopherol, (vitamin E), tocopherol sorbate, tocopherol acetate, other esters of tocopherol, butylated hydroxy benzoic acids and the like. A preservative may be selected form $C_{12}$ to $C_{15}$ alkyl benzoates, alkyl p-hydxoxybenzoates, ascorbic acid, benzalkonium chloride, sorbic acid, citric acid, benzoic acid, benzoic acid esters of $C_9$ to $C_{15}$ alcohols, chlorocresol, methyl paraben, propyl paraben, sodium benzoate and the like.

In some embodiments, the drug loaded nano-resin particles are formulated into oral dosage forms. The oral dosage form may be a solid oral or a liquid oral dosage form suitable for peroral, sublingual or buccal delivery. The present invention in one aspect provides use of a solid oral dosage form comprising drug loaded nanoresin particles having a particle size distribution characterized in that the $D_{90}$ value is between 200 nanometers to 900 nanometers and $D_{10}$ value is not less than 50 nanometers and pharmaceutically acceptable excipients. The solid oral dosage form may be in the form of a capsule, a tablet, an ovule, a chewable tablet, a buccal tablet, a sublingual tablet, a quick-dissolving tablet, a mouth disintegrating tablet or granules, an effervescent tablet, a granule, a pellet, a bead, a pill, a sachet, a sprinkle, a film, a dry syrup, a reconstitutable solid, a lozenge, a troche, an implant, a powder, a triturate, a platelet, or a strip. The dosage forms are formulated using suitable pharmaceutically acceptable excipients. The solid oral dosage forms according to the present invention may comprise pharmaceutically acceptable excipients suitable for oral dosage forms such as those mentioned in the book—Remington: The Science and Practice of Pharmacy, $22^{nd}$ Edition. These include, but are not limited to diluents, disintegrating agents, bulking agents, binders, lubricants, glidants, colouring agent etc.

In one embodiment, the present invention provides nano-resin particles suitable for pharmaceutical use, wherein the resin particles have a particle size distribution such that $D_{90}$ value is between 200 nanometers to 900 nanometer and $D_{10}$ value is not less than 50 nanometers, and is prepared by a process comprising the steps of:
i. washing an ion exchange resin and suspending in an aqueous liquid,
ii. subjecting the suspension of (i) to wet milling for a period such that the particles have a particle size distribution characterized in that the $D_{90}$ value is between 200 nanometers to 900 nanometers and $D_{10}$ value is not less than 50 nanometers,
iii. subjecting the suspension of (ii) to purification to achieve impurities within acceptable limit,
iv. drying the purified suspension to obtain nano-resin particles in the form of dry powder, having a water content of not more than 15%.
wherein the water extractable impurities are not more than 1% by weight of the resin and the organic impurities are not more than 3 ppm.

In one embodiment, the nano-resin particles according to the present invention are prepared by a process comprising the steps of—
i. washing an ion exchange resin and suspending in an aqueous liquid,
ii. subjecting the suspension of (i) to wet milling for a period such that the particles have a particle size distribution characterized in that the $D_{90}$ value is between 200 nanometers to 900 nanometers and $D_{10}$ value is not less than 50 nanometers,
iii. subjecting the suspension of (ii) to purification to remove the water extractable and organic impurities,
iv. drying the purified suspension to obtain nano-resin particles in the form of dry powder.

In one preferred embodiment, the purification of the suspension to remove the water extractable and organic impurities is performed by diafiltration technique with the help of use of a membrane filter having a pore size molecular weight cut off in the range of 200 kD to 750 kD, such as 250, 300, 350, 400, 450, 500, 550, 600, 650 or 700 kD, preferably in the range of 300 kD to 600 kD.

In one specific embodiment, the step of wet milling is performed in two steps comprising:
(a) milling the resin of step (i) using grinding medium having bead size that range from 0.5 mm to 1.25 mm, and
(b) milling the resin of sub-step (a) using grinding medium having bead size that range from 0.1 mm to 0.4 mm.

In one embodiment the grinding medium has a bead size in the range approximately 0.5 mm to 1.25 mm, such as 0.6 0.7, 0.8, 0.9, 1.0, 1.1 or 1.2 mm.

In one embodiment the grinding medium has a bead size in the range approximately 0.1 mm to 0.4 mm, such as 0.2 or 0.3 mm.

In one specific embodiment, the nano-resin particles according to the present invention are prepared by a process comprising the steps of—
i. washing an ion exchange resin and suspending in an aqueous liquid,
ii. subjecting the suspension of (i) to wet milling for a period of time such that particles have a particle size distribution characterized in that the $D_{90}$ value is between 200 nanometers to 900 nanometers and $D_{10}$ value is not less than 50 nanometers, wherein the wet milling is performed in two sub-steps comprising (a) milling the resin of step (i) using grinding medium having bead size that range from 0.5 mm to 1.25 mm, and (b) milling the resin of sub-step (a) using grinding medium having bead size that range from 0.1 mm to 0.4 mm,
iii. subjecting the suspension of (ii) to diafiltration, using a ultrafiltration membrane having a pore size molecular weight cut off in the range of 200 kD to 750 kD, to remove the water extractable and organic impurities,
iv. lyophilizing the suspension of (iii) to obtain free flowing nano-resin particles in the form of dry powder.

In one aspect, the step of washing the marketed micron size resin (step (i)) may be carried out by using a suitable organic liquid like methanol, which leads to removal of extraneous organic materials. For this, the resin suspension in water is taken and methanol is added to the resin suspension along with stirring of the suspension for about 10 to 15 minutes. The suspension is kept on standing for 15-20 minutes, to allow settling down of the particles, followed by decantation of the supernatant. This washing process may be then repeated 3-4 times. The resulting resin particles may be then washed multiple times with hot water (about 80-90° C.) by following a similar process, until the pH of water wash reach below 7.5.

In one aspect, the step of wet milling (step ii) may be carried out by use of a wet milling equipment, such as NETZSCH mill, DeltaVita 600 or similar wet milling machines or grinding mills. The beads used for milling, i.e. the milling medium beads may be made up of zirconium oxide or glass or similar material. In this step, the washed resin obtained as per step (i) is subjected to wet milling for a period of time sufficient to achieve the target particle size of $D_{90}$ between 200 nms to 900 nms and $D_{10}$ of less than 50 nms. The milling is carried out for a period of time varying from about 2 hours to about 48 hours, preferably from about 4 hours to 24 hours, such as 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23 or 23.5 hours, more preferably from about 5 hours to 20 hours. To carry out wet milling, a slurry of the resin particles (about 10%) in an aqueous medium such as water for injection is taken in milling chamber of the wet milling machine (such as NETZSCH, DeltaVita 600 mill) along with grinding media beads (such as Zirconium oxide beads of suitable sizes) followed by wet milling of the resin particles.

In a preferred embodiment, the step of wet milling is carried out in two-steps, first using grinding medium having beads of a higher size, followed by using grinding medium having beads of size smaller than that used in first step.

In one embodiment, the step of wet milling is performed in two steps comprising: (a) milling the resin of step (i) using grinding medium having bead size that range from 0.5 mm to 1.25 mm, and (b) milling the resin of sub-step (a) using grinding medium having bead size that range from 0.1 mm to 0.4 mm.

In some embodiments, in step (a), the wet milling is carried out using a grinding medium having bead of size in the range of 0.5 mm to 1.25 mm, for a period of time varying from 1 hour to 10 hours, such as 2, 2.5, 3.0, 3.5, 4.0, 4.5, 5.0, 5.5, 6.0, 6.5, 7.0, 7.5, 8.0, 8.5, 9.0 or 9.5 hours and in step (b), the wet milling is carried out using grinding medium having bead of size in the range of 0.1 mm to 0.4 mm, for a period of time varying from about 2 hour to 15 hours, such as 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0 or 14.5 hours. The period of milling may vary depending upon certain factors like the weight of resin to be milled, the type of machine etc.

In one particular embodiment, having batch size of 2 kg resin particles, the particle size reduction can be carried out using a grinding medium having bead of size 0.5 mm for a period of time of about 5.5 hours, followed by milling by using grinding medium of size 0.3 mm for a period of time of about 7.0 hours.

This forms nano-resin particles having desired particle size such that $D_{90}$ value is between 200 nms to 900 nms and $D_{10}$ value is less than 50 nms. The process preferably involves use of two different size grinding media, which advantageously leads to reduction in particle size to nano range in a shorter period of time and the particles size achieved is smaller as compared when single size grinding media is used. In some embodiments, the method of preparing nano-resin particles of the present invention do not include techniques like emulsion polymerization, suspension polymerization or precipitation polymerization techniques.

Post milling, the milled resin suspension is subjected to a step of purification by techniques like diafiltration, ultrafiltration and the like. Due to milling, the level of water extractable impurities and organic impurities in the nano-resin suspension rise to levels higher than the desired limits.

The step of purification by diafiltration results in nano-resins particles that are pure and have impurities within desired limits.

In one preferred embodiment, the wet milled suspension is subjected to diafiltration, wherein the milled resin suspension obtained in step (ii) is subjected to ultrafiltration and concentration using a ultrafiltration membrane having a molecular weight in the range of 200 kD to 750 kD. This leads to removal of water extractable and organic impurities, thus resulting in the formation of purified nano-resin particles. The ultrafiltration membranes suitable for this purpose include membrane fibre cartridges having a molecular weight in the range of 200 kD to 750 kD, preferably in the range of 300 to 500 kD Post purification step, the purified nano-resin suspension is dried. The step of drying the suspension may be carried out by suitable techniques such as freeze drying, lyophilization etc. In one preferred embodiment, the purified suspension of nano-resins is dried by lyophilization to form a dried powder comprising nano-resin particles. The water content of the dried powder is not more than 15%, preferably not more than 10%, more preferably not more than 5% by weight, for example 1%, 2%, 3%, 4%, 5%, 6%, 7%, 8%, 9% or 10% by weight of the resin.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Any embodiments specifically and explicitly recited herein may form the basis of a disclaimer either alone or in combination with one or more further embodiments.

While the present invention is disclosed generally above, additional aspects are further discussed and illustrated with reference to the examples below. However, the examples are presented merely to illustrate the invention and should not be considered as limitations thereto.

Example 1

Preparation of nanoresin: The method of preparation of the nano-resin according to the present invention comprises the steps of washing the ion exchange resin, wet milling the washed resin, preferably using two different size grinding media's, followed by diafiltration. According to one embodiment of the present invention, the nano-resin was prepared by method given below.

Step (i): Washing: The marketed micron size resin Amberlite IRP 69 resin (obtained from Rohm and Haas, France) was washed with methanol to ensure removal of extraneous organic material. The resin was taken in a SS vessel and methanol was added. The resin suspension was stirred for about 10 to 15 minutes. The particles were then allowed to settle down for 15-20 minutes and the supernatant was decanted. The washing process was repeated 3-4 times. The above material was then washed multiple times with hot water for injection (80-90° C.) by following similar process till the pH of water wash reached below 7.5.

Step (ii): Wet milling—The wet milling was carried out using NETZSCH, DeltaVita 600 wet milling machine. A 10% slurry of the resin particles in an aqueous medium such as water for injection was passed though the milling chamber containing Zirconium oxide beads of suitable size as grinding media. Wet milling was then carried out in two stages. Particularly, in step 1, the particle size reduction was carried out using grinding media of size 0.5 mm for about 5.5 hours. In sub-step 2, the particle size reduction was carried out by using grinding media of size 0.3 mm for about 7 hours. This results in formation of nano-resin particles having desired particle size i.e. $D_{90}$ value is between 200 nanometers to 900 nanometers and $D_{10}$ value is not less than 50 nanometers.

Step (iii): Polishing—In this step, the milled resin suspension obtained in step (ii) was filtered from 10μ polypropylene capsule filter, (HDC II, KAJ1100P1) under stirring to make suspension with uniform particle size and to remove any agglomerates and residual larger particles. The particle size remains same after and before filtration.

Step (iv): Purification by diafiltration—The milled resin suspension obtained in step iii above was found to be pale yellow, likely due to the water extractable impurities or organic impurities generated during the process, and this may render it un-suitable for pharmaceutical use in this form. The water extractable impurities were measured in unmilled resin and in the permeate after milling. It was found that during the milling process the water extractable impurity was increased (Table 1). Similarly the content of organic impurities also increased (Table 3).

The milled nano-suspension obtained in step (ii) as a result of wet milling was subjected to diafiltration wherein ultrafiltration and concentration of the milled resin suspension was carried out using an Ultrafiltration membrane system consisting of 300 kD to 500 kD hollow fiber cartridge/membrane. The milled resin suspension was diafiltered and washed with water for injection until the permeate was almost clear and absorbance (measured using a UV spectrophotometer at 650 nm) was reduced below 0.02 AU. The processing step leads to purification of nano-resin suspension, wherein the content of water extractable and organic impurities is reduced and complies with the set specification, the absorbance of permeate reduces to below 0.02 AU and the permeate appearance becomes clear. The table 2 gives the results of absorbance of the permeate, before and after the diafiltration step. The value of absorbance reduced to 0.003 post diafiltration step, from 0.04 (before diafiltration).

The level of water extractable impurity in the milled suspension was estimated by measuring the weight of the water soluble impurities extracted in the permeate by diafiltration and determining the percentage by weight of the weight of total milled resin taken for diafiltration.

The level of water extractable impurity was reduced after washing and complies with the set specification (<1%). The Table 1 represents the level of water extractable impurity before and after the diafiltration step. The content of water extractable impurity was reduced to 0.88 post diafiltration step, from 2.96 (before diafiltration). The reduced values post diafiltration complies with the set specification.

TABLE 1

Results of water extractable impurity

|  | Specification | Unmilled Resin suspension | Nano resin suspension after milling | Nano resin suspension after diafiltration |
|---|---|---|---|---|
| Water Extractable Impurity (% w/w) | <1.0% | 0.06 | 2.96 | 0.88 |

TABLE 2

Results of absorbance

| Sr. No. | Sample | Absorbance |
|---|---|---|
| 1 | Extract of Milled resin before diafiltration | 0.040 |
| 2 | Extract of milled resin after diafiltration cycle. | 0.003 |

Figure 1:
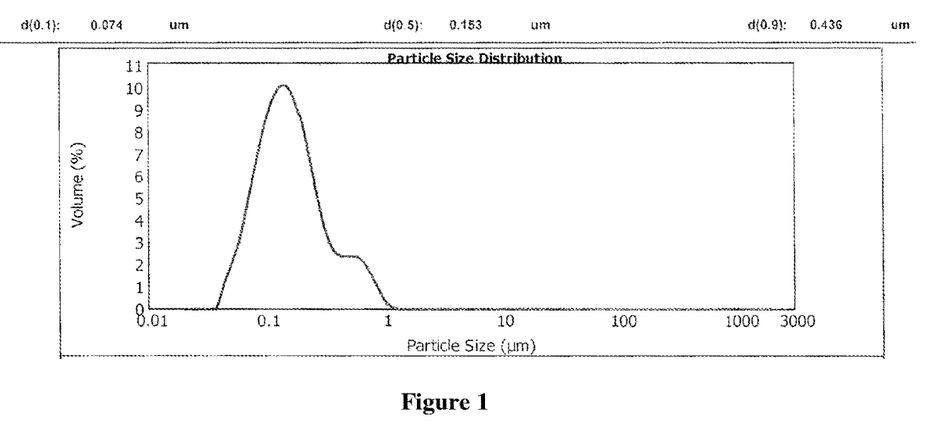
FIG. 1 is an illustrative histogram for the nano-resin particles of the present invention.

The concentrated milled resin suspension was analyzed for particle size. It was observed that the particle size, was such that the $D_{90}$ value is between 200 nanometers to 900 nanometers and $D_{10}$ value is not less than 50 nanometers. Specifically, in one batch, the particle size distribution of the nano-resin particles obtained by following the aforementioned process was such that $D_{90}$ value was 436 nms (0.436μ), $D_{50}$ value was 153 nms (0.153μ), and $D_{10}$ value was 74 nms (0.074μ). The histogram of the particle size distribution is presented in FIG. 1. In another batch, prepared following same process, the nano-resin particles have particle size distribution characterized in that $D_{90}$ value was 315 nms (0.315μ), $D_{50}$ value was 147 nms (0.147 μ), and $D_{10}$ value was 73 nms (0.073μ).

The nano-resins were also analyzed for content of organic impurities, such as individual unknown and total unknown organic impurities, by HPLC technique. The HPLC analysis was performed using dichloromethane as diluent and reference standard solutions of styrene RS, diethylbenzene RS, naphthalene RS, divinylbenzene RS and p-xylene RS and DB-624, J & W as chromatographic column. The results are presented in Table 3. Based on the results, surprisingly it was found that Individual unknown and total unknown impurities were increased and not complying the specifications (<1 ppm and <3 ppm respectively) when the resin was milled to nano-size of $D_{90}$ between 200 nanometers to 900 nanometers and $D_{10}$ of not less than 50 nanometers. When milled resin suspension was subjected to Diafiltration using water and ultrafiltration membrane system, the Individual unknown and total unknown impurities were reduced and complied with specification. The content of organic impurities in milled resin before and after diafiltration are presented below in Table 3:

TABLE 3

Results of Organic impurities in milled resin powder

| Organic impurities | Unmilled resin | Milled resin | Milled resin obtained after step of purification |
|---|---|---|---|
| Individual unknown impurity | Below Qualification limit, <0.03 ppm | 6 ppm | Not detected, 0 ppm |

TABLE 3-continued

Results of Organic impurities in milled resin powder

| Organic impurities | Unmilled resin | Milled resin | Milled resin obtained after step of purification |
|---|---|---|---|
| Total unknown impurity | Below Qualification limit, <0.03 ppm | 13 ppm | Not detected, 0 ppm |

The milled nano-resin suspension was subsequently lyophilized. It was analyzed for water content. The water content was found to be 4.06% by weight. The milled resin was stored in bulk for further use in formulating pharmaceutical dosage form.

Example 2

Biological Reactivity Test: The nanoresin prepared according to Example 1 was subjected to in-vivo and in-vitro biological reactivity tests to determine the biological reactivity. The tests are given below:

1. In-Vivo Biological Reactivity: The in-vivo biological reactivity of milled resin extract was assessed by Intracutaneous test in New Zealand White Rabbits. Extraction of Amberlite IRP 69 was done in 1 in 20 solution of alcohol in 0.9% sodium chloride solution as per procedure mentioned in USP <88> Biological reactivity, in-vivo. It was observed that the milled nano-resin extract complied with USP "Intracutaneous test" by biological reactivity study.

2. In vitro Biological Reactivity: The in-vitro biological reactivity of milled resin extract was assessed by Agarose diffusion Assay in NCTC clone 929 (L cell; L-929) ATCC. No biological reactivity of mammalian cell cultures following milled resin extract was observed.

Example 3

The present example provides a particular embodiment of the present invention wherein the nano-resin particles were loaded with an anti-glaucoma drug brimonidine and the drug-loaded nanoresin particles were formulated into an aqueous suspension dosage form suitable for ophthalmic use:

TABLE 4

Aqueous suspension of Brimonidine Tartrate

| Ingredients | Ingredients Function | % w/v |
|---|---|---|
| Brimonidine Tartrate | Active ingredient | 0.35 |
| Amberlite IRP 69 | Resin | 0.35 |
| Hydroxy propyl methyl cellulose | Polymeric vehicle | 0.3 |
| Polyvinylpyrrolidone |  | 1.2 |
| Carbopol 974P (carbomer) |  | 0.1 |
| Benzalkonium Chloride | Preservative | 0.02 |
| Edetate Disodium | Chelating agent | 0.1 |
| N-Lauroylsarcosine sodium | Preservative | 0.06 |
| Mannitol | Osmotic agent | 4.5 |
| Tromethamine q.s to adjust pH to 7.4 | pH adjusting agent | 0.32 |
| Water for Injection | Vehicle | q.s. |

Process: Hydroxy propyl methyl cellulose was dispersed with high speed in warm water for injection along with stirring to obtain uniform dispersion. In another container, polyvinylpyrrolidone K-90 was added and dispersed in water for injection with stirring to obtain uniform dispersion. Further, a dispersion of carbopol 974P in water for injection was prepared and neutralized with tromethamine (pH 7.4). The hydroxy propyl methyl cellulose and povidone polymeric dispersions obtained above were added sequentially to the carbopol 974P phase. The polymer mixture was autoclaved at 121° C. for 20 minutes. N-lauryl sarcosine sodium was mixed in a portion of water for injection and added to the polymer phase after filtration through 0.2 micron nylon filter. Mannitol was dissolved in a portion of water for injection at 50-60° C. and to this, benzalkonium chloride and edetate disodium were added to form a clear solution. This solution was added to the above polymer phase.

The nano-sized resin particles (of Amberlite IRP 69) were prepared as per Example 1. The particles has a particle size distribution such that $D_{90}$ value is 606 nms (0.606μ), $D_{50}$ value is 240 nms (0.240μ), and $D_{10}$ value of 148 nms (0.148μ), were dispersed in water for injection and sterilized by autoclaving at 121° C. for 20 minutes. To this sterilized resin dispersion, a solution of brimonidine tartrate in water for injection, which was filtered through 0.2 micron and 0.45 micron nylon filter, was added and stirred. This drug loaded nano-resin particles aqueous dispersion was added to the polymer mixture along with stirring and homogenization. The pH was adjusted with tromethamine solution to about 7.4.

Example 4

The drug loaded nano-resin particles in suspension dosage form as described in Example 3, forms reversible clusters. The instant example demonstrates the effect of shear on these reversible clusters of drug loaded nano-resin particles suspended in Example 3, which decluster into individual drug-loaded nano-resin particles when subjected to shear, such as a shear resulting from blinking in the eye. This effect was measured in terms of particle size distribution, initially and upon application of shear.

Procedure: The test samples were subjected to shear by placing the vials containing the suspension on bath sonicator (Model type: MC-109 and SI no-1909; Mfg. by Oscar Ultrasonic Pvt. Ltd.) and shear was applied in the form of sonication frequency of 33±3 kHz for 5 seconds and the sample was withdrawn to measure the particle size distribution. Following intervals of 1 minute each the process is repeated 5 times and each time the particle size was measured.

The particle size measurement was done using Malvern Mastersizer 2000, Ver.5.60, Malvern Instruments Ltd., Malvern, UK but the analyser's sonication means were not used. The sample was only subjected to mild stirring by a mechanical stirrer. The observations are summarized below in Table 5.

TABLE 5

Effect of shear on the particle size distribution of the resin particles:

| | PSD* | Volume mean diameter in microns recorded by Malvern lazer diffraction method | | | | | |
|---|---|---|---|---|---|---|---|
| | | Initial | 1 min | 2 min | 3 min | 4 min | 5 min |
| Example 3 | $D_{10}$ | 0.852 | 0.475 | 0.338 | 0.151 | 0.145 | 0.140 |
| | $D_{50}$ | 19.549 | 13.882 | 0.996 | 0.254 | 0.229 | 0.213 |
| | $D_{90}$ | 58.970 | 49.111 | 30.405 | 1.398 | 0.512 | 0.449 |

PSD*—Particle Size Distribution in Volume mean diameter in microns

Figure 2:
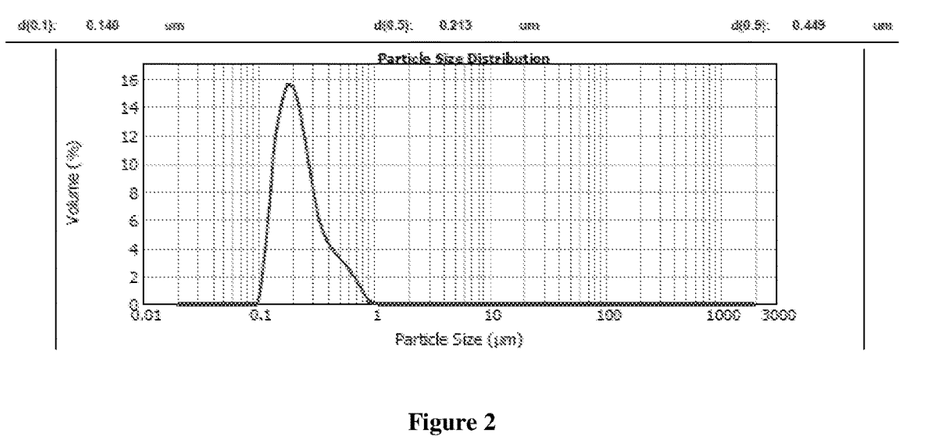
FIG. 2 is the histogram showing particle size distribution of individual drug-loaded nanoresin particles in aqueous suspension when subjected to application of shear as per Example 4 of the specification.

Observations: It was found that clusters of drug loaded nano-resin particles of Example 3, disintegrated completely as shear was applied to the suspension. This was evident by the decrease in the particle size observed upon application of shear/sonication as shown in Table 5. The $D_{50}$ of drug-resin nanoparticles was initially about 19.5 microns, which upon application of shear at regular interval for 5 minutes disintegrated and converted into individual drug-resin nanoparticles having $D_{50}$ of 0.213 micron (213 nm). The histograms of the particle size distribution of the drug-loaded nano-resin particles after application of shear at 5 minute is represented by FIG. 2. It corresponds to particle size distribution upon application of shear at 5 minutes and represents largely individual nano-resin particles and particle size distribution of the individual drug loaded nano-resin particles.

Example 5

The present example provides safety test of aqueous suspension dosage form prepared according to one embodiment of the present invention. The aqueous suspension dosage form (of Example 3) was subjected to safety studies by daily ocular administration of the suspension formulation for consecutive 14 days. The following protocol was followed:

Twenty New-Zealand White rabbits; (10 males and 10 females) were randomized, based on body weights, into following five study groups. Each group comprised of two animals of both gender. The desired dose was administered by ocular instillation.

G1 (saline {control}, 360 μL/animal/day), 30 μL per eye/time ×6 times a day

G2 (Placebo, 360 μL/animal/day), 30 μL per eye/time ×6 times a day

G3 (Low dose {test}, 60 μL/animal/day), 30 μL per eye/time ×1 times a day

G4 (Mid dose {test}, 180 μL/animal/day); 30 μL per eye/time ×3 times a day

G5 (High dose {test}, 360 μL/animal/day) 30 μL per eye/time ×6 times a day

G3, G4 & G5 test=0.35% w/v Brimonidine Tartrate Aqueous Suspension of the present invention (Example 3)

The test parameters which were evaluated included—Daily Clinical Signs and Mortality; Detailed Clinical Sign Observation; Body Weights; Ophthalmoscopy and Necroscopy. The details of these test parameters along with the results are described below. Besides this, other parameters which were also evaluated include: clinical pathology, histology, biochemistry, prothrombin time and urine analysis.

Daily Clinical Signs and Mortality—Cage side observations were done, twice daily, for all animals to note clinical signs, adverse effects; including those for eyes, morbidity and mortality during the dosing period. These observations were performed once before dosing and post last dosing between 2-4 hours. Animal check to observe mortality was performed twice daily throughout study period and findings were recorded. No mortality was observed in control, placebo as well as in test item dosed groups. During dosing period of 14 days, yellowish exudates (probably clearing of excess test item) staining the areas around both eyes was observed in G4 and G5. No other adverse clinical signs were observed.

Detailed Clinical Sign Observation—Detailed observations were performed before initiation of dosing and on Days 1, 7 and 14 post dosing. The animals were examined closely for clinical signs, general behavior or any other signs. Eyes were examined with hand-held slit lamp ophthalmoscope and findings were recorded according to Draize scoring system described in table 6 below:

TABLE 6

Clinical Sign Observation-

| Corneal Opacity: degree of density (the area of corneal opacity noted) (maximum possible 4) | |
|---|---|
| No ulceration or opacity | 0 |
| Scattered or diffuse areas of opacity, details of iris clearly visible | 1 |
| Easily discernible translucent area, details of iris slightly obscured | 2 |
| Nacrous area, no details of iris visible, size of pupil barely discernible | 3 |
| Opaque area, iris not discernible through the opcity | 4 |
| Iris (maximum possible 2) | |
| Normal | 0 |
| Markedly deepened rague, congestion, swelling, moderate circumcorneal hyperaemia, or injection, any of these or combination of any thereof it is still reacting to light (sluggish reaction possible) | 1 |
| No reaction to light, hemorrhage, gross destruction (any or all of these) | 2 |
| Conjuctivae (maximum possible 3) | |
| Redness (refers to palpebral and bulbar conjunctivae, excluding corneas and iris) | |
| Normal | 0 |
| Some blood vessels definitely hyperae ic (injected) | 1 |
| Diffuse, crimson colour, individual vessels not easily discernible | 2 |
| Diffuse beefy red | 3 |
| Chemosis: Swelling (refers to lids and/or to nictitating membranes) (Maximum possible 4) | |
| Normal | 0 |
| Some swelling above normal | 1 |
| Obvious swelling with partial eversion of lids | 2 |
| Swelling with lids about half closed | 3 |
| Swelling with lids more than half closed | 4 |

During detailed clinical sign observation, no test item related adverse clinical signs were observed in any group throughout the study period. Detailed examination of eyes (including Draize scoring) did not show any adverse finding/sign. The scoring for all the animals in all groups was zero.

Ophthalmoscopy: Ophthalmoscopy was performed in all animals at initiation of dosing; thereafter it was performed on Days 7 and 14. At each observation, both eyes of animal were examined with hand held ophthalmoscope (Ophthalmoscope Heine). Observations for following were noted: Eye ball, Lacrimation, Conjunctivae, Eyelids, Sclera, Pupil reaction to light, Cornea, Iris, Anterior chamber, Lens, Vitreous body and Fundus with use of mydriatic agent. The Fluorescein-staining of cornea was done at the end of dosing on Day 14. Examination of cornea was performed with the help of ophthalmoscope.

During ophthalmoscopy, no abnormality was detected in the eye of any animal during pre-dose and on Day 7 and 14 at post-dosing. No signs of corneal damage or any other abnormality was noticed for cornea with fluorescein strip staining.

Necroscopy—On completion of dosing, all animals from G1 to G5 were necropsied on day 15. Gross pathology was noted. The cranial, thoracic and visceral cavities were opened and examined macroscopically. Eye balls, optic nerve and adnexal tissues (eyelids, accessory glands, nictitating membrane, conjunctivae and orbital muscles) were examined grossly for any macroscopic change. Microscopic evaluation of tissues were performed in G1, G2 and G5 and it was not extended to any lower group since no test item related histopathological adverse effect was noted in G5. Brain, liver, lung with main stem bronchi were peer reviewed in all animals from G1, G2 and G5.

At terminal necropsy, statistically significant increase in absolute heart weights of G2 males, relative spleen weight in G4 males and relative adrenal weight in G4 females was noted; however, these changes were not dose depended, hence not considered as test item related adverse effect. Microscopic evaluation of organs/tissues in G2 or G5 male and female animals did not show any finding that could be related to dosing of placebo or test item. The microscopic findings observed in G2 and G5 were those of incidental/spontaneous nature and comparable to that in G1. Microscopic examination of eye and its adnexal tissues/organs did not show any test item or placebo related findings.

In summary—No mortality was observed for males and females of any dose group. During dosing period, yellowish exudates staining around the eyes was observed both in G4 and G5 which probably was due to clearing out of excess test item. No test item related clinical signs were observed during daily or detailed clinical sign observations. No test item related adverse changes noticed in body weights, percent body weight changes, ophthalmoscopy, hematology, biochemistry, urine, absolute organ weights and relative organ weights of males and females. In males and females, no test item related macroscopic or microscopic lesions were observed in any organ including eyes in any dose group.

The drug loaded nano-resin particles according to the present invention not only provides an improved efficacy in terms of reduction of intraocular pressure but is also found to be safe without any adverse effects when administered for prolonged period of time, such as 14 days or more.

Example 6

Long term safety profile of suspension of Example 3, after multiple daily instillation for 30 consecutive days in New Zealand white rabbits, was evaluated. Particularly, the hemodynamic parameters were assessed. For this, the study design was as follows: Group 1 received 30 µL per eye 6 times a day (n=6) and group 2 received the suspension of Example 3 as 30 µL per eye/time ×6 times a day (n=6).

Hemodynamic parameters were recorded for all animals at pre-dose, Day 15 and at the end of dosing period at Day 30. These parameters included Electrocardiogram (ECG); BP, Pulse rate, $SpO_2$, Respiratory rate and Temperature.

Summary of observations: No test item related changes were noticed for hemodynamic parameters in any animal during the study period. No mortality was observed in any dose group. During dosing period, in G2 group, a slight yellowish exudate staining around both eyes was observed (which was probably due to flowing-out of excessive test item). No test item related changes were noticed in detailed clinical sign observations, body weights, percent body weight changes, ophthalmoscopy, hematology and biochemistry of animals. Therefore, based on these observations, the ocular NOAEL (no observed adverse effect levels) of 0.35% w/v Brimonidine tartrate ophthalmic suspension, according to one embodiment of the present invention, is established to be about 0.33 mg/kg/day in New Zealand White Rabbits. The NOAEL for systemic effects is also established to be 0.33 mg/kg/day. This is about 30 times more than the human maximum dose in mg/m$^2$ basis.

It is concluded that ocular delivery of test item at 30 µL/eye in both eyes, up to maximum 6 times per day for 30 days consecutive daily administration did not produce any adverse effects in the eye, with no local toxicity at the site of application as well as no systemic toxicity.

Thus, the ophthalmic dosage form comprising the drug loaded nano-resin particles according to the present invention not only provides an improved efficacy in terms of reduction of intraocular pressure but is also found to be safe without any adverse effects when administered for prolonged period of time, such as 30 days or more.

Example 7

The example provides a suspension formulation of Doxycycline, according to one embodiment of the present invention.

TABLE 7

Aqueous suspension dosage form of doxycycline Hydrochloride

| Ingredients | Ingredients function | Quantity % |
|---|---|---|
| Doxycycline Hyclate (eq to Doxyclycline 0.05%) | Active ingredient | 0.057 |
| Sodium polystyrene sulphonate (Amberlite IRP 69) | Resin | 0.019 |
| Hydroxy propyl methyl cellulose | Polymeric vehicle | 0.3 |
| Polyvinylpyrrolidone | | 1.2 |
| Carbopol 974P (carbomer) | | 0.1 |
| Benzalkonium Chloride | Preservative | 0.02 |
| Edetate Disodium | Chelating agent | 0.1 |
| N-Lauroylsarcosine sodium | Preservative | 0.06 |
| Mannitol | Mannitol | 4.5 |
| Tromethamine q.s to adjust pH to 5.0 | pH adjusting agent | 0.0248 |
| Water for Injection | Vehicle | q.s. to 100 |

Process: Hydroxy propyl methyl cellulose was dispersed with high speed in a warm water for injection stirring to obtain uniform dispersion. To it polyvinylpyrrolidone (povidone K-90) was dispersed in water for injection with stirring to obtain uniform dispersion. Further, carbopol 974P dispersion in water for injection, neutralized with tromethamine (pH 7.4), was prepared. The hydroxy propyl methyl cellulose and povidone polymeric dispersions obtained above were added sequentially to the carbopol 974P phase. The polymer mixture was autoclaved at 121° C. for 20 minutes. Further, other excipients like mannitol, benzalkonium chloride, n-lauryl sarcosine and edetate disodium were added sequentially to above polymer phase and stirred until dissolved and form a clear solution.

The nano-sized resin particles (of Amberlite IRP 69) prepared as per Example 1, having $D_{90}$ value of 436 nms (0.436μ), $D_{50}$ value of 153 nms (0.153μ), and $D_{10}$ value of 74 nms (0.074μ), were dispersed in water for injection and sterilized by autoclaving at 121° C. for 20 minutes. To this sterilized resin dispersion, a solution of doxyclycline hyclate in water for injection, which was filtered through 0.2 micron and 0.45 micron nylon filter, was added and stirred. This drug loaded nano-resin particles aqueous dispersion was added to the polymer mixture along with stirring and homogenization. The pH was adjusted with tromethamine solution to about 7.4. The aqueous suspension formulation of Doxycycline is suitable for delivery of drug via dermal or oral or sublingual or ophthalmic route of administration.

Example 8

The example provides a suspension formulation of Asenapine maleate, according to one embodiment of the present invention.

TABLE 8

Asenapine maleate suspension

| Ingredients | Quantity (% w/v) |
|---|---|
| Asenapine Maleate | 1.5 |
| Sodium polystyrene sulphonate (Amberlite IRP 69) | 1.5 |
| Water for Injection | q.s. to 100 |

Asenapine maleate was dissolved under stirring in warm water. Ion exchange resin of Example 1, having $D_{90}$ value of 436 nms (0.436μ), $D_{50}$ value of 153 nms (0.153μ), and $D_{10}$ value of 74 nms (0.074μ), was dispersed in a portion of water for injection heated at 60° C. with stirring. The asenapine maleate solution was added to the resin dispersion and allowed to cool it at room temperature under stirring. The so formed suspension was dried under pressure, to obtain a free flowing powder. This drug loaded nano sized ion exchange resin particles were lubricated with a lubricant and were filled into a hard gelatin capsule, suitable for per-oral ingestion and delivery of drug in the GIT.

Example 9

The example provides aqueous suspension formulation of Bromfenac sodium, according to one embodiment of the present invention.

TABLE 9

Bromfenac sodium suspension 0.07% w/v

| Ingredient | Function Ingredients | Example 9 (A) % w/v | Example 9 (B) % w/v |
|---|---|---|---|
| Bromfenac sodium (equivalent to bromfenac free acid 0.07%) | Active Ingredient | 0.0805 | |
| Indion ™860 | Anion exchange resin | 0.07 | |
| Carbopol 974 P (Carbomer) | Polymeric | — | 0.1 |
| Hydroxy propyl methyl cellulose | vehicle | 0.3 | |
| polyvinylpyrrolidone | | 1.2 | |
| Benzalkonium Chloride | Preservative | 0.02 | |
| Edetate Disodium | Chelating agent | 0.1 | |
| N-Lauroylsarcosine sodium | Preservative | 0.06 | |
| Mannitol | Osmotic agent | 4.5 | |
| Tromethamine | pH adjusting agent | qs to adjust pH to 7.8 | |
| Water for Injection | Vehicle | q.s. to 100 | q.s. to 100 |

Process: In a stainless steel (SS 316) beaker, about 15% water for injection of total batch size was taken and heated to 85° C. The specified polymeric vehicle, such as hydroxy propyl methyl cellulose (hypromellose 2910) was dispersed with high speed stirring to obtain uniform dispersion. The stirring was continued till temperature reached 25° C. In another stainless steel (SS 316) beaker, about 12% water for injection of total batch size was taken at 25° C. Polyvinylpyrrolidone (povidone K-90) was dispersed in water for injection with stirring to obtain uniform dispersion. In case of Example 9 (B) a portion of water for injection was taken and heated at about 65° C. Carbopol 974P was dispersed in water for injection with stirring. The stirring was continued till the temperature reached 25° C. The Carbopol 974P slurry was neutralized (pH 7.4) with tromethamine. The hypromellose and povidone polymer dispersions obtained above were added sequentially to the carbopol 974P phase. The polymer mixture was autoclaved at 121° C. for 20 minutes. N-lauryl sarcosine sodium was mixed in a portion of water for injection and added to the polymer phase after filtration through 0.2 micron nylon filter. Mannitol was dissolved in a portion of water for injection at 50-60° C. and benzalkonium chloride, and edetate disodium were added to form a clear solution. This solution was added to the above polymer phase. A portion of water for injection of total batch size was taken in a vessel and Indion™860 obtained following a process similar to Example 1, was dispersed with stirring. This dispersion was autoclaved at 121° C. for 20 minutes. In another vessel, a portion of water for injection was taken and bromfenac sodium was added with stirring to dissolve. This solution was filtered through 0.2 micron and 0.45 micron nylon filter. Filtered bromfenac sodium solution was added to above autoclaved Indion™860 dispersion and stirred for 30 minutes.

The Indion™860 & bromfenac sodium dispersion was added to the polymer mixture obtained above with stirring and stirring was continued for about 30 minutes to 1 hour. The volume of suspension was finally made up to 100% batch size. The suspension was stirred for about 60 minutes, followed by homogenization at 15000 rpm for 10 mins. The pH was adjusted with tromethamine solution to about 7.8. The aqueous suspension formulation of bromfenac is suitable for ophthalmic use. The aqueous suspension formulation may also be used for delivery of drug via dermal or oral or sublingual route of administration.

Example 10

According to one embodiment of the present invention, this example provides a suspension formulation of Asenapine maleate having asenapine nano-resin complex, which is subsequently formulated into a Tablet dosage form for per oral delivery.

TABLE 10

Asenapine maleate nanoresin suspension 1.0% w/v

| Ingredients | Ingredient Function | Quantity % |
| --- | --- | --- |
| Asenapine (eq. to Asenapine maleate) | Active | 1.0 (eq. to 1.41) |
| Sodium polystyrene sulphonate (Amberlite IRP 69) | Cation exchange Resin | 1.0 |
| Water for Injection | Vehicle | q.s. to 100 |

Process: The resin sodium polystyrene sulfonate (Amberlite IRP 69) was processed and obtained as per Example 1. The particle size distribution of the milled resin was such that $D_{10}$=0.134 microns, $D_{50}$=0.198 microns and $D_{90}$=0.351 microns. The nanoresin (Amberlite IRP 69) so obtained was dispersed in a portion of water for injection and heated at 60° C. to 70° C. with stirring. Asenapine (in the form of a salt Asenapine maleate) was dissolved in water for injection under stirring at 60° C. to 70° C. This Asenapine maleate solution was added to the resin dispersion at heated condition with stirring and then allowed to cool at room temperature under stirring. The volume of suspension was finally made up to 100% batch size. Asenapine-resin complex Suspension was washed with water by centrifugation at 2000 rpm for 50-60 min and then lyophilized to obtain dried powder.

TABLE 11

Tablet dosage form comprising asenapine nano-resin complex:

| Ingredient | Ingredient Function | Quantity (mg/tablet) |
| --- | --- | --- |
| Asenapine-Amberlite IRP69 complex | Drug with carrier | 10 (Both drug and resin in equivalent quantity) |
| Mannitol | Diluent | 47.3 |
| Crosspovidone ultra | Disintigrant | 10.5 |
| Aerosil - Colloidal Silica | Glidant | 3.5 |
| Magnesium stearate | Lubricant | 0.7 |
| Sucralose | Sweetener | 0.5 |

Dried powder of Asenapine-nano resin complex prepared as above was mixed with mannitol, crosspovidone ultra, aerosil (colloidal silica) and sucralose and blended manually. Magnesium stearate was then mixed with the blend and final powder was homogenously mixed. The blend was compressed to yield white to off white round biconvex uncoated tablet plain on both sides by direct compression method. The solid tablet dosage form is suitable for per-oral administration.

Example 11

This example provides a suspension formulation comprising Amitriptyline nano-resin complex, which is subsequently formulated into a topical dosage form i.e. gel.

TABLE 12

Amitriptyline nano-resin suspension 1.0% w/v

| Ingredients | Function | Quantity % |
| --- | --- | --- |
| Amitriptyline (eq. to Amitriptyline hydrochloride) | Active | 1.0 (eq. to 1.21) |
| Sodium polystyrene sulphonate (Amberlite IRP 69) | Cation exchange Resin | 1.0 |
| Water | Vehicle | q.s. to 100 |

Process: Sodium polystyrene sulfonate (Amberlite IRP 69) was processed and obtained as per Example 1. The particle size distribution of the milled resin was such that $D_{10}$=0.134 microns, $D_{50}$=0.198 microns and $D_{90}$=0.351 microns. The Amberlite IRP 69 nanoresin so obtained was dispersed in a portion of water for injection at room temperature with stirring. In a stainless steel (SS 316) beaker, water for injection was taken at room temperature. Amitriptyline used in the form of a salt. Amitriptyline hydrochloride was dissolved under stirring. The Amitriptyline hydrochloride solution was added to the resin dispersion at room temperature under stirring. The volume of suspension was finally made up to 100% batch size. Amitriptyline-resin complex suspension was washed with water by centrifugation at 2000 rpm for 5-10 min and then lyophilized to obtain dried powder.

TABLE 13

Topical gel composition comprising Amitriptyline nano-resin complex:

| Ingredients | Function | Quantity (% w/w) |
| --- | --- | --- |
| Amitriptyline-Amberlite IRP69 complex | Active with carrier | 4.0 (Both drug and resin in equivalent quantity) |

TABLE 13-continued

Topical gel composition comprising Amitriptyline nano-resin complex:

| Ingredients | Function | Quantity (% w/w) |
|---|---|---|
| Carbomer homopolymer Type B (Carbopol 974P) | Formulation base | 1.0 |
| Sodium hydroxide | pH adjusting agent | 0.012 |
| Water | Vehicle | q.s. |

Process: In a stainless steel (SS 316) beaker, water for injection was taken and heated to 65° C. The specified polymeric vehicle, Carbopol 974P was dispersed in heated water for injection with stirring. The stirring was continued till the temperature reached 25° C. The Carbopol 974P slurry was neutralized with sodium hydroxide. Separately dried powder of amitriptyline-nanoresin complex prepared as above was suspended in a portion of water. This suspension was mixed with neutralized Carbopol 974P gel with stirring by glass rod. pH of the resulting topical gel formulation was adjusted to 5.0 to 5.5. The gel formulation is suitable for dermal application.

Example 12

TABLE 14

Topical gel formulation of Methotrexate.

| Ingredients | Ingredient Function | Quantity % w/w |
|---|---|---|
| Methotrexate sodium | Active Ingredient | 1-10 |
| Indion 860 | Resin | 1-10 |
| Hydroxy propyl cellulose | Thickening agent | 5 |
| Edetate Disodium | Chelating agent | 0.1 |
| Polyethylene glycol 400 | Emollient | 10 |
| Butylated hydroxyl toluene | Stabilizer | 0.05 |
| Oleic acid | Penetration enhancer | 2.5 |
| Triethanolamine | pH adjusting agent | qs |
| Water for Injection | Vehicle | q.s. to 100 |

Process: Hydroxy propyl cellulose was dispersed in heated water for injection with stirring. Edetate disodium, polyethylene glycol 400, butylated hydroxyl toluene, oleic acid, triethanolamine were dissolved in water for injection sequentially and stirred until dissolved and form a clear solution. This solution was added to the above polymer phase.

The Indion 806 nano-resin prepared by step similar to Example 1, was dispersed in a portion of water for injection with stirring. In another vessel, methotrexate sodium was dissolved in water with stirring and filtered. The filtered methotrexate sodium solution was added to above dispersion of Indion 806 nano-resin particles and stirred for 30 minutes. The dispersion was subjected to diafiltration and washing with water for injection. This slurry was lyophilized to get the dry powder which was then added to the polymer mixture obtained above with stirring which results in formation of gel. The gel was stirred for 60 minutes. The gel formulation is suitable for topical application, such as dermal application to the skin.

Example 13-14

Examples 13-14 provides topical ointment formulation of Methotrexate and Minocycline.

TABLE 15

| | | Quantity % w/w | |
|---|---|---|---|
| Ingredients | Function | Example 13 | Example 14 |
| Minocycline Hydrochloride | Active Ingredient | 1-5 | — |
| Methotrexate Sodium | Active Ingredient | — | 1-10 |
| Sodium polystyrene sulphonate (Amberlite IRP 69) | Resin | 1-5 | — |
| Indion 860 | Resin | — | 1-10 |
| Mineral oil | Emollient | 10 | 10 |
| Glyceryl mono oleate | Stabilizer | 1 | 1 |
| White petrolatum | Ointment base | Qs to 100 | Qs to 100 |

Process: The Amberlite IRP 69 nano resin/Indion 860 nano-resin was obtained by a process similar to Example 1. The resin was dispersed in a portion of water for injection with stirring. In another vessel, drug (minocycline hydrochloride/methotrexate sodium) was dissolved in water for injection with stirring and filtered. The filtered drug solution was added to above resin dispersion and stirred for 30 minutes. The dispersion was subjected to diafiltration and washing with water for injection and the resulting slurry was lyophilized to get the dry powder. White petrolatum was taken in a beaker and heated it at 70-80° C. In another beaker, the drug-resin complex was taken along with mineral oil and glyceryl mono oleate and properly mixed at temperature 50-70° C. This phase was added to the white petrolatum phase and stir continuously for 1 hour, which results in formation of ointment, suitable for topical drug delivery. The gel formulation is particularly suitable for dermal application to the skin, or drug delivery to the otic or nasal cavity.

The invention claimed is:

1. A topical pharmaceutical composition comprising an ionisable drug adsorbed on to the surface of ion exchange nano-resin particles wherein
    (i) the nano-resin particles have a particle size distribution characterized in that the $D_{90}$ value is between 200 nanometers to 900 nanometers and $D_{10}$ value is not less than 50 nanometers,
    (ii) the nano-resin particles contain water extractable impurities of not more than 1% by weight of the total resin, and
    (iii) the nano-resin particles contain total unknown organic impurities of not more than 3 ppm.

2. The pharmaceutical composition as claimed in claim 1, wherein nano-resin particles have the particle size distribution characterized in that the $D_{50}$ value is between 75 nanometers to 300 nanometers.

3. The pharmaceutical composition as claimed in claim 1, wherein the nano-resin is selected from a cation exchange resin or an anion exchange resin.

4. The pharmaceutical composition as claimed in claim 1, wherein the pharmaceutical composition is an aqueous suspension comprising the drug adsorbed ion exchange nano-resin particles, a suspending agent and an aqueous vehicle.

5. The pharmaceutical composition as claimed in claim 4, wherein nano-resin particles have the particle size distribution characterized in that the $D_{50}$ value is between 75 nanometers to 300 nanometers.

6. The pharmaceutical composition as claimed in claim 4, wherein the ionisable drug is brimonidine.

7. The pharmaceutical composition as claimed in claim 4, wherein the ionisable drug is brimonidine tartrate.

8. A method of treating a disease, comprising topically administering a pharmaceutical composition of claim 1.

9. The method as claimed in claim 8, wherein the nano-resin particles have the particle size distribution characterized in that the $D_{50}$ value is between 75 nanometers to 300 nanometers.

10. The method as claimed in claim 8, wherein the nano-resin particles contain water extractable impurities of not more than 1% by weight of the total resin.

11. The method as claimed in claim 8, wherein the nano-resin particles contain total unknown organic impurities of not more than 3 ppm.

12. The method as claimed in claim 8, wherein the nano-resin is selected from a cation exchange resin or an anion exchange resin.

13. The method as claimed in claim 8, wherein the pharmaceutical composition is an aqueous suspension dosage form comprising a suspending agent and an aqueous vehicle.

14. The method as claimed in claim 8, wherein the pharmaceutical composition is a semisolid dosage form in an aqueous or a non-aqueous vehicle and the drug is delivered via dermal route of administration.

15. The method as claimed in claim 14, wherein the semisolid dosage form is a cream, ointment, lotion, emulsion, suspension or a gel.

\* \* \* \* \*